(12) United States Patent
Olsen

(10) Patent No.: US 7,166,119 B2
(45) Date of Patent: Jan. 23, 2007

(54) SCISSORS FOR CUTTING NARROW CURVES

(75) Inventor: Hans Olsen, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/518,707

(22) PCT Filed: Jun. 19, 2003

(86) PCT No.: PCT/DK03/00406

§ 371 (c)(1),
(2), (4) Date: Dec. 22, 2004

(87) PCT Pub. No.: WO2004/002336

PCT Pub. Date: Jan. 8, 2004

(65) Prior Publication Data

US 2005/0203556 A1    Sep. 15, 2005

(30) Foreign Application Priority Data

Jun. 27, 2002    (DK) ............................... 2002 01009

(51) Int. Cl.
*A61B 17/32* (2006.01)
(52) U.S. Cl. ........................ 606/174; 30/194
(58) Field of Classification Search ................ 606/174, 606/167, 138, 118, 51, 205; 30/120, 146, 30/194, 257, 225, 248, 341, 286, 356; 112/294, 112/297; 7/135, 134; 33/631; 56/241
See application file for complete search history.

(56) References Cited

U.S. PATENT DOCUMENTS 973,296 A * 10/1910 Peddle ......................... 30/233
1,956,587 A * 5/1934 Parker et al. ................. 30/349
2,619,965 A * 12/1952 Goldstone .................... 606/118
2,873,526 A    2/1959 Visconti
3,084,433 A * 4/1963 Kimmel ....................... 30/254
4,819,636 A    4/1989 Gerich et al.
4,924,574 A    5/1990 Jones et al.
5,074,046 A    12/1991 Kolesky
5,079,843 A    1/1992 Shelton et al.

FOREIGN PATENT DOCUMENTS

WO    WO 95/31144    11/1995

* cited by examiner

*Primary Examiner*—(Jackie) Tan-Uyen Ho
*Assistant Examiner*—Natalie Pous
(74) *Attorney, Agent, or Firm*—Jacobson Holman PLLC

(57) ABSTRACT

A pair of scissors has two elements that are cross-wise rotationally movably assembled in a hinge, each of said elements consisting of a blade and an arm. The arms each terminate in a ring for a user's finger. The general direction of the blades and the arms in a closed position of the scissors is making an angle large enough to place both rings on the same side of an extension line of the general direction of the blades. The blades are curved and have different lengths and heights, the upper blade being the shorter and higher and optionally provided with a protruding nose part, and the lower blade is relatively narrow and provided with a bulb shaped tip and a chamfered and/or rounded inner edge said distal end of said back edge of said upper blade has a nose part protruding a distance (n1) from the distal end of the cutting edge of the upper blade and having a distance (n2) from the cutting edge of the lower blade in a closed position of the scissors.

20 Claims, 2 Drawing Sheets

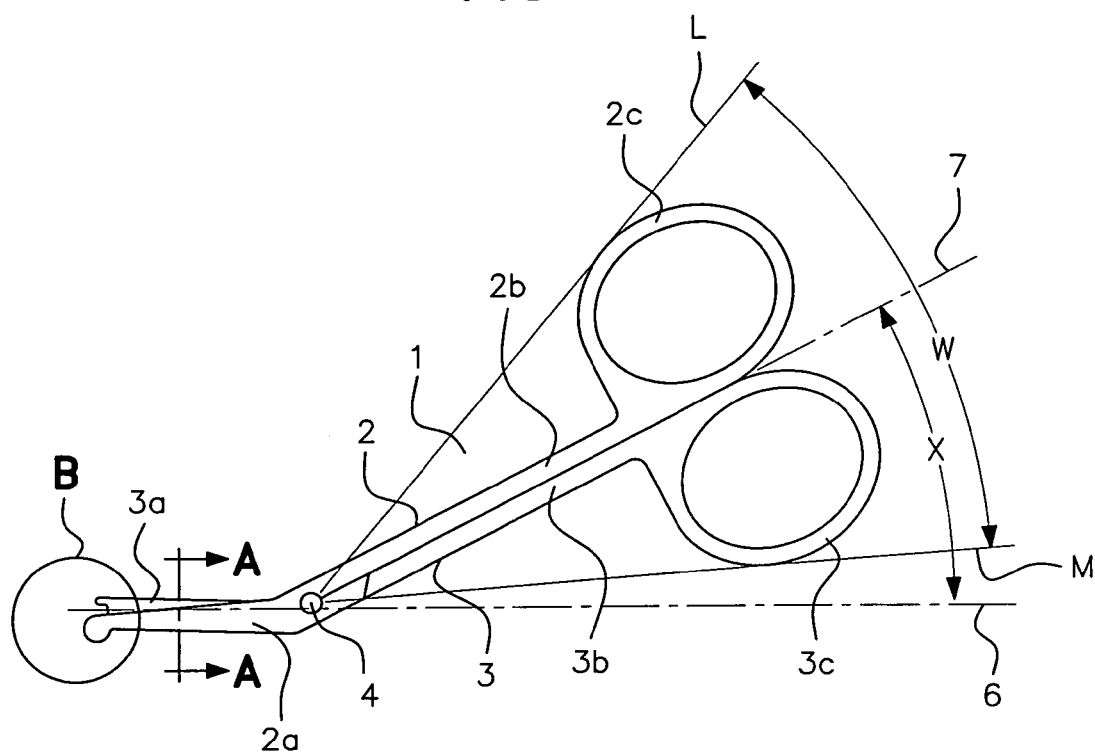
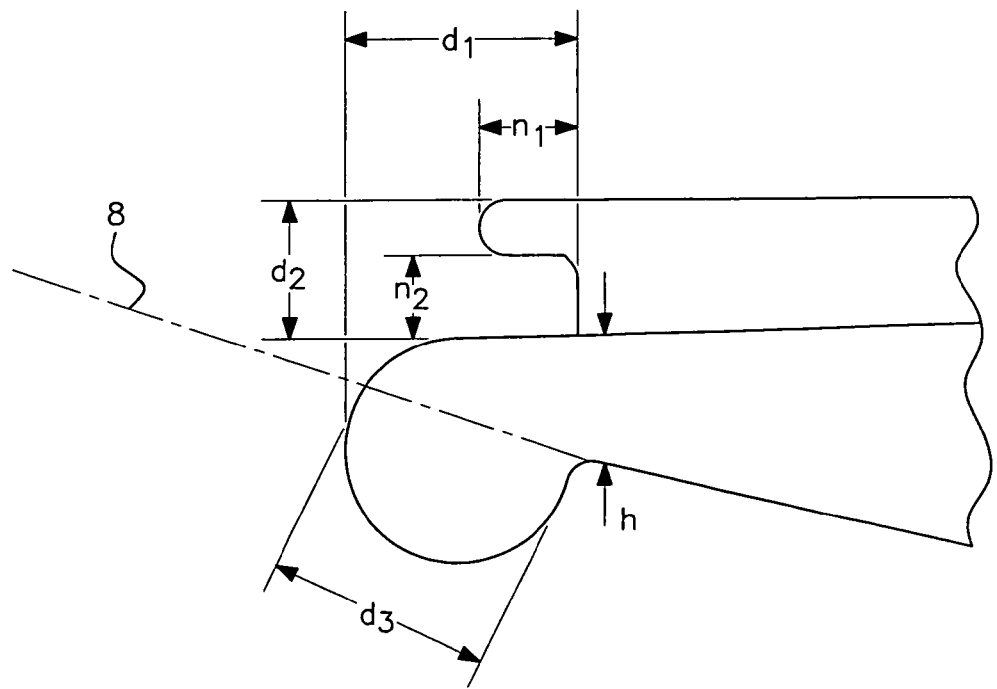

SCISSORS FOR CUTTING NARROW CURVES

This is a nationalization of PCT/DK03/000406 filed Jun. 19, 2003 and published in English.

BACKGROUND OF THE INVENTION

1. Field of the Invention

The present invention relates to a pair of scissors for cutting shape involving narrow curves as when adapting the shape and size of a hole in a soft, laminated material like a body side ostomy member of an ostomy appliance having a centrally placed hole for accommodating a stoma to fit the stoma optimally.

In connection with surgery for a number of diseases in the gastro-intestinal tract a consequence is, in many cases that the patient is left with an abdominal stoma such as a colostomy, an ileostomy or a urostomy. In such cases or in connection with a fistula the patient will have to rely on an appliance to collect the bodily material emerging from such opening.

Ostomy appliances are well known. Such appliances may be two-piece or one-piece appliances. In both types of appliances, a body side member is attached to the wearer's abdomen, and optionally a receiving member or bag is attached to the body side ostomy member for receiving secretions from the ostomy in case of a two-piece appliance.

When using one-piece appliances, the whole appliance, including the adhesive wafer or pad securing the appliance to the skin is removed and replaced by a fresh appliance. When using two-piece appliances, the body side ostomy member is left in place for several days, and only the receiving member or bag is replaced.

The service time of the body side ostomy member depends on the amount and aggressiveness of the secretions and of the tightness between the stoma and the body side ostomy member more so, as the access of aggressive secretions to the skin is causing skin problems.

The tightness between the stoma and the body side ostomy member depends on an accurate adaptation of the size and the shape of the hole in the body side member to the size and shape of the stoma.

2. Description of the Related Art

Many attempts have been made designing devices in order to ease the cutting of holes in body side ostomy members.

One principle is shown in U.S. Pat. No. 4,924,574 in which the device comprises a base having a flat top surface which receives the wafer flat-wise thereon in a predetermined position relative to a gage which is engageable by a circular cutter that cuts a circular opening or hole in the centre of the wafer, the diameter of the hole corresponding to a prior measurement of the diameter of the particular stoma. Variants of this principle, which enables cutting of non-circular holes are also known Another principle is shown in U.S. Pat. No. 5,079,843 in which the ostomy wafer is placed between the bottom face of a cylindrical body mounted with a blade and a base plate whereupon the blade cuts into the wafer and the circular hole cut as the cutter is rotated. Adjustment of the blade's distance from the center of the cylindrical body for cutting different sized holes is accomplished by means of removable adjustment spacers.

Most of the devices dedicated to adapt a hole in a body side ostomy member to a stoma are quite large and heavy, and also in many cases expensive, so as a consequence many ostomates rely on an ordinary pair of scissors to adapt the hole in the body side member.

In some instances, a pair of scissors intended for cutting finger nails are used, as they have a convenient size, and also have curved blades, which eases the cutting of circular holes. Other users prefer scissors intended for use in connection with fine sewing, as they have more pointed and narrower blades yielding more precision when cutting.

U.S. Pat. No. 2,873,526 discloses a pair of scissors for cutting bandages and the like wherein the scissors has arms forming an angle with the blades and wherein the upper and lower blades have different length and the lower blade is longer than the upper and the lower blade has a nose for preventing damage on the underlying surfaces. The scissors disclosed in U.S. Pat. No. 2,873,526 does not comprise measures, which prevents that the upper blade pass under the surface of the bandage when the scissors is fully closed.

However, cuffing of materials like adhesive wafers presents a number of problems encountered during the cutting process, which are not addressed by the known types of scissors, so there is still a need for a proper tool for this purpose.

SUMMARY OF THE INVENTION

The invention relates to a pair of scissors having two elements rotationally movably assembled in a hinge, the orientation of said elements being generally crossed and in a plane essentially perpendicular to the axis of said hinge and said movement of said elements relative to each other from a closed position to an open position taking place in said plane, each of said elements consisting of a blade and an arm, said blades and said arms having hinge ends defined by said hinge and distal ends, said blades being an upper blade and a lower blade in a position of use, said blades having cutting edges and back edges, each of said arms terminating in a ring for accommodating a finger of the user, said rings in a closed position of the scissors defining an outer angle with said hinge as the centre.

BRIEF DESCRIPTION OF THE DRAWINGS

The invention is disclosed more in detail with reference to the drawings in which FIG. 1 is showing a pair of scissors of the invention seen from the side, FIG. 2 is showing an enlargement of the encircled part designated B of FIG. 1.

DETAILED DESCRIPTION OF THE PRESENT INVENTION

Figure 3:
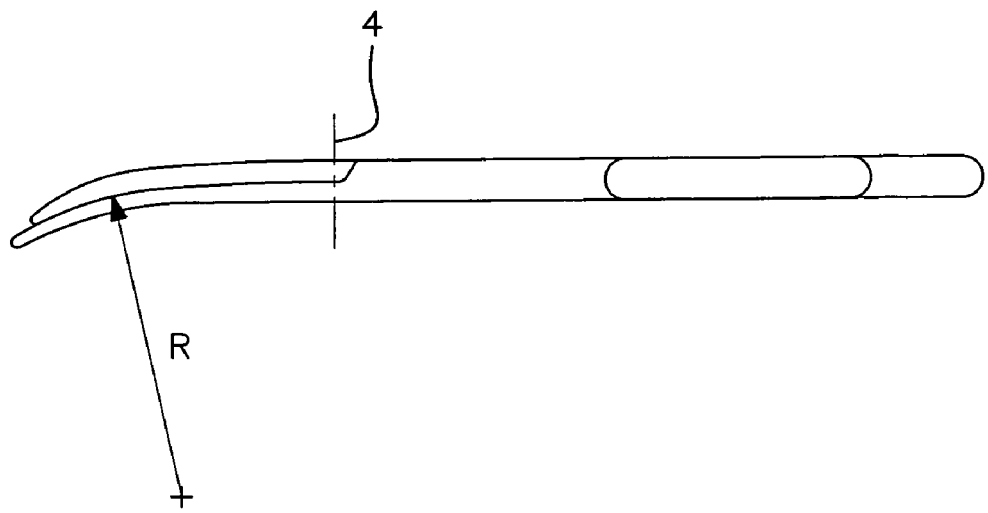
FIG. 3 is showing a pair of scissors of the invention seen from above.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention relates to a pair of scissors for adapting the size of a hole in a material having physical characteristics like those of an ostomy wafer, which pair of scissors consists of two elements rotationally movably assembled in a hinge, the orientation of said elements being generally crossed and in a plane essentially perpendicular to the axis of said hinge and said movement of said elements relative to each other from a closed position to an open position taking place in said plane, each of said elements consisting of a blade and an arm, said blades and said arms having hinge ends defined by said hinge and distal ends, said blades being an upper blade and a lower blade in a position of use, said blades having cutting edges and back edges, each of said arms terminating in a ring for accommodating a finger of the user, said rings in a closed position of the scissors defining an outer angle defined by lines from said hinge point as tangents to said rings, wherein said blades have a general direction represented by a line, wherein said arms have a general direction indicated by a line defined as the bisecting line of said angle, said lines forming an angle large enough to place both of said rings entirely on the same side of an extension of said direction line of said blades, wherein said blades are curved and wherein said distal end of said back edge of said upper blade has a nose part protruding a distance (n1) from the distal end of the cutting edge of the upper blade and having a distance (n2) from the cutting edge of the lower blade in a closed position of the scissors Ostomy wafers normally have a significant thickness in the area in which the hole is to be cut and this thickness presents other problems in process of cutting holes in the wafer.

The thickness provides the wafer with a significant rigidity, so that ordinary symmetrical scissors are difficult to use. It has therefore proven an advantage to make the scissors in an angular layout so that a first line between the hinge point and the distal end of the blades and a second line from the hinge point to a contact point between said rings in a closed position of the scissors make an angle large enough to place both of said rings entirely on the same side of an extension of the first line, whereby the cutting process can be performed with the fingers operating the scissors moving freely above the surface of the wafer without having to force a bending of the wafer otherwise necessary.

One of the problems is experienced during cutting when the scissors are closed completely, in which situation there is a substantial risk that the distal ends of the blades will both end up being on the same side of the material to be cut, thereby compromising a continuing of the cutting. It has been found, that if the cutting edge of the upper blade is shorter than the lower blade, the lower blade is prevented from leaving the lower side of the material when the scissors are closed, i.e. the distal ends of the blades are prevented from being both on the upper side of the material. To address the opposite situation, i.e. in order to prevent the distal end of the upper blade to get caught under the lower surface of the material, the height of the distal end of the upper blade may be made larger than the thickness of the material to be cut. In this way, a guiding of the upper blade by the slit already cut can ensure an easy lifting of the upper blade from the closed position to an open position. A further prevention against the upper blade dipping under the material to be cut is achieved, if the back edge of the upper blade on the distal end has a nose part protruding over the cutting edge of the upper blade. The nose part is substantially narrower than the height of the distal end of the upper blade in order not to squeeze the material to be cut when the scissors are completely closed.

The thickness of the material to be cut may cause the lower edge of the lower blade of a normal pair of scissors to have a tendency to deform the edge of the newly cut part of the hole when continuing cutting a circular hole. When both blades are given a curved shape as known from scissors for nail cutting this tendency can be reduced. The curve should give the blades a bend towards the side of lower blade, which, for use by right-handed users, would give to a bend to the left when seen from the user during use, but a mirrored version for use by left-handed users as well as a pair of scissors wherein both rings are below the material to be cut is within the scope of the invention.

In order to further facilitate cutting of narrow curves, at least the lower blade of the scissors is advantageously made low and narrow as in e.g. scissors for sewing work. However, as there is a substantial risk of damaging the pouch when cutting one-piece appliances if the lower blade is pointed as is the case for scissors for sewing work, the lower blade is advantageously provided with a bulb-shaped distal end, thereby at the same time protecting the pouch and the user and still keeping the working part of the blade narrow for easing the cutting of narrow curves. Furthermore, it has been found, that if the lower edge of the lower blade is rounded and chamfered on the side facing the upper blade, the tendency of this edge of the lower blade to ruin or at least impair a clean cut can be almost eliminated or, when cutting very narrow curves, significantly reduced.

The thickness of an ostomy wafer combined with the relatively soft centre of the adhesive between the plastics films may result in unwanted deformation of the adhesive near the cut, and to alleviate this, one or both of the cutting edges of the blades are preferably given an angle to ease penetration of the cutting edge through the wafer.

Ostomy wafers normally are provided with various sorts of plastic film on the outer surfaces of the adhesive and as these films may be relative hard and also often have a very smooth surface, there is a risk of the scissors slipping on the surface, thereby jeopardizing the cutting process. It may therefore be advantageous to provide one or both of the cutting edges of the blades with a non-slip surface, e.g. rough sand blasting or grinding, the latter preferably made in a transverse direction of the blades.

DESCRIPTION OF THE PREFERRED EMBODIMENTS

The invention is now explained more in detail with reference to the drawings showing preferred embodiments of the invention.

Reference is made to FIG. 1 which shows a pair of scissors generally designated (1) of the invention for adapting the size of a hole in a material having the physical characteristics of an ostomy wafer, said scissors consisting of two elements (2, 3) rotationally movably assembled in a hinge (4), the orientation of said elements being generally crossed and in a plane essentially perpendicular to the axis of said hinge and said movement of said elements relative to each other from a closed position to an open position (not shown) taking place in said plane, each of said elements consisting of a blade (2a, 3a) and an arm (2b, 3b), said blades and said arms having hinge ends defined by said hinge and distal ends, said blades being an upper blade and a lower blade in a position of use, said blades having cutting edges and back edges, each of said arms terminating in a ring (2c, 3c) for accommodating a finger of the user, said rings in a closed position of the scissors defining an outer angle (W) defined by lines (L, M) from said hinge point (4) as tangents to said rings. A line (6) representing the general direction of the blades and a line (7), indicating the general direction of the arms (2b, 3b) defined as the bisecting line of said angle (W), are shown. Lines (6) and (7) intersect in the hinge point at an angle (X), which in the embodiment shown is large enough to place both of said rings entirely on the same side of an extension of said first line in a closed position of the scissors. In a more preferred embodiment, said side is the upper side of a material to be cut in a position of use of the scissors. The size of a suitable angle obviously depends on the sizes of the rings (2c, 3c) for the fingers and the general size of the scissors. In a preferred embodiment, the relation between the length of the blades and the length of the arms is at least 1:1, more preferred at least 1:1.5, and even more preferred at least 1:2, which relation has been found to result in sufficiently low cutting forces and allow for a high precision in the cutting. In this embodiment, it has been found that the size of the angle (X) should be at least 20° and up to 45° or even more for cutting thicker materials and more preferred about 35°. In the embodiment shown, the rings (2c, 3c) are of the same almost circular shape, but other shapes of rings may be used. Both rings, and especially the lower ring (3c) may be of a different, longer shape for accommodating more than one finger and the scissors may, if desired, be asymmetric and adapted for use by right or left handed users.

FIG. 2 is showing in a larger scale the portion designated (B) of the distal ends of the blades of the scissors shown in FIG. 1, defining a difference of lengths (d1) between the cutting edge of the upper blade and the lower blade, a height (d2) with which the distal end of the back edge of the upper blade stands above the cutting edge of the lower blade and a nose part of the distal end of the back side of the upper blade protruding a distance (n1) from the distal end of the cutting edge of the upper blade and having a distance (n2) from the cutting edge of the lower blade in a closed position of the scissors. A difference of lengths (d1) of at least 0.5 mm, more preferred between 1 and 5 mm or even more for cutting thicker materials, preferably about 3 mm, has been found adequate for use with most commonly known ostomy wafers, but a difference of lengths significantly larger, i.e. up to 20 mm may be convenient when cutting larger holes in materials being difficult to cut, e.g. very thick materials. For the upper blade, it has been found, that if the distal end of the upper blade stands at least 0.5 mm, more preferred at least 1.5 mm and preferably at least 2.7 mm above the cutting edge of the lower blade, cutting of most of the known ostomy wafers can be performed easily, but the distal end of the upper blade may stand even as high as 20 mm above the cutting edge of the lower blade if necessary when cutting very thick materials. The protrusion (n1) of the nose part over the cutting edge of the upper blade should be at least 0.5 mm, suitably at least 1 mm, and the distance (n2) between the nose part and the cutting edge of the lower blade at least 0.3 mm, suitable at least 0.5 mm, when the scissors are completely closed but depending on the general size of the scissors and the material to be cut the protrusion (n1) may be up to 15 mm and the distance (n2) may be up to 15 mm.

The lower blade is generally shaped as if it would end in a point like scissors use for fine sewing work as indicated by the dotted line (8). However, in order to prevent damage to the user or a pouch of an ostomy appliance of which the wafer is to be cut, the end of the lower blade is provided with a bulb-like tip with a general diameter (d3), which bulb implies that the lower blade has a minimum height (h) at or near the bulb. The diameter of the bulb (d3) and the minimum height (h) are to some extent functionally interrelated and also should relate to the overall size of the scissors. The diameter of the bulb (d3) is preferably be at least 0.5 mm to secure prevention of damage to e.g. the pouch. At the same time, in order not to compromise cutting of narrow curves, the diameter of the bulb is preferably not substantially larger than the difference of length of the two blades, preferably around 3.5 mm but bulb diameters up to 10 mm may be convenient when cutting larger holes.

Referring to FIG. 3, the curving of the blades is shown as seen from above in a position of normal use. The curve is represented by a mean radius, (R). The radius (R) of the curve may be from 15 mm to 200 mm depending on the material and the size of the holes to be cut and in a preferred embodiment the radius is from 20 to 60 mm, and is preferably about 40 mm. It is understood, that the curves of the two blades are mutually adjusted to preserve a proper cutting functionality.

Figure 4:
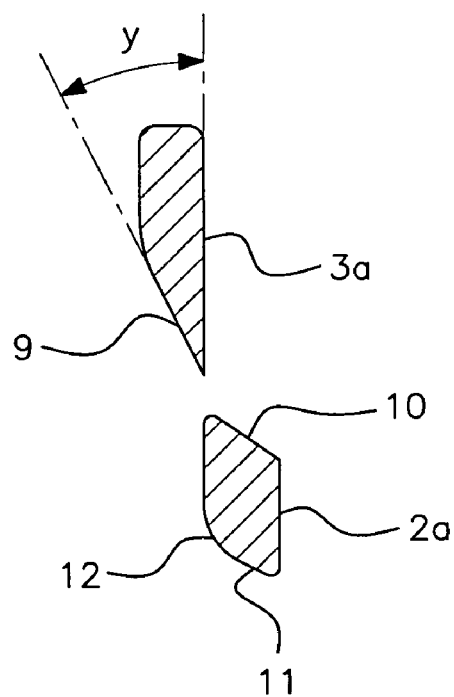
FIG. 4 is showing a section along the line A—A in FIG. 1.

FIG. 4 shows a section of the scissors of FIG. 1 along the line A—A with the upper and lower blades (2a, 3a) having cutting edges (9, 10). In this embodiment, the inner side of the lower edge of the lower blade has a chamfer (11) and a rounding (12). The chamfer may vary from 0° to about 60° and the rounding may vary from 0 mm to a radius corresponding to about twice the actual thickness of the lower blade. The sizes of chamfer and rounding may be adapted to suit the material and the sizes of holes to be cut, but a preferred embodiment may have a chamfer of at least 15° and up to 45° more preferred about 30° and a rounding varying from 2 mm at the hinge end to 0.5 mm at the point of minimum height.

Also in FIG. 4, the cutting edge (9) of the upper blade makes an angle (Y) with the general plane of the scissors, which angle may be between 75° and 15°, preferably between 20° and 50°, and in a more preferred embodiment the angle is about 30°. If the material to be cut indicates the need, of course also the lower blade may be angled correspondingly.

One or both of the cutting edges (9,10) may advantageously be provided with a non-slip surface, e.g. rough sand blasting or grinding, the latter preferably made in a transverse direction of the blades. In a preferred embodiment, the non-slip surface is a series of transverse sharp ridges with a height of approximately 0.25 mm along the cutting edge of the upper blade, but ridges as low as 0.02 mm and larger ridges up to 1.5 mm may be useful when cutting thinner or thicker materials respectively.

The invention has been described in relation to ostomy wafers having a relatively hard and smooth surface and a softer core, but would be equally suited for cutting other soft, laminated materials presenting similar problems when cut, like e.g. wound dressings or even cardboard materials.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A pair of scissors comprising two elements rotationally movably assembled in a hinge, the orientation of said elements being substantially in a first plane essentially perpendicular to the axis of said hinge and said movement relative to each other from a closed position to an open position taking place substantially in said first plane, each of said elements having a blade and an arm, said blades and said arms having hinge ends defined by said hinge and distal ends, said blades being an upper blade and a lower blade in a position of use, said blades having cutting edges and back edges, each of said arms terminating in a structure configured to accommodate a finger of the user, both of said blades being curved out of said first plane such that said cutting edges are curved sideways relative to said arms, said back edge of said upper blade being straight along a second plane substantially perpendicular to said first plane when said scissors are in a closed position, said back edge having a distal end with a nose part in line therewith and protruding a first distance from the distal end of the cutting edge of the upper blade, said nose part having a lower surface generally parallel with said straight back edge and spaced a second distance from, and in a direction generally perpendicular to, the cutting edge of the lower blade in said closed position of the scissors.

2. The pair of scissors according to claim 1 wherein a distal edge of said upper blade below said nose and extending said second distance is oriented to be substantially perpendicular to said upper blade back edge.

3. The pair of scissors according to claim 1 wherein said upper and lower blades have a difference of lengths, the lower blade being the longer blade.

4. The pair of scissors according to claim 1 wherein said structure for accommodating the user's finger on each of said two arms is a ring, said rings in a closed position of the scissors defining a first angle defined by lines from said hinge point as tangents to said rings, said blades having a general direction represented by a first line, said arms having a general direction indicated by a second line defined as the bisecting line of said first angle, said lines making a second angle large enough to place both of said rings entirely on the same side of an extension of said first direction line of said blades.

5. The pair of scissors according to claim 1 wherein a main part of said lower blade tapers toward said distal end which is provided with a rounded bulb.

6. The pair of scissors according to claim 5, wherein said bulb is joined with said tapered main part at a point generally aligned with a base of said nose part in a closed position of the scissors.

7. The pair of scissors according to claim 1 wherein said back edge of said lower blade is provided with a chamfer inwardly.

8. The pair of scissors according to claim 1 wherein said back edge of said lower blade is provided with an inwardly placed rounding.

9. The pair of scissors according to claim 1 wherein at least one of said cutting edges is provided with a non-slip surface.

10. The pair of scissors according to claim 1 wherein at least one of said cutting edges makes an angle of less than 75° with said plane.

11. A pair of scissors comprising two elements rotationally movably assembled in a hinge, the orientation of said elements being substantially in a first plane essentially perpendicular to the axis of said hinge and said movement relative to each other from a closed position to an open position taking place substantially in said first plane, each of said elements having a blade and an arm, said blades and said arms having hinge ends defined by said hinge and distal ends, said blades being an upper blade and a lower blade in a position of use, said blades having cutting edges and back edges, each of said arms terminating in a structure configured to accommodate a finger of the user, both of said blades being curved out of said first plane such that said cutting edges are curved sideways relative to said arms, said upper blade having a straight back edge along a second plane substantially perpendicular to said first plane when said scissors are in a closed position, said upper blade and being shorter than said lower blade, a distal end of said straight back edge having a nose part in line therewith and protruding a first distance from the distal end of the cutting edge of the upper blade, and said lower blade having a length extending beyond said nose part in said closed position of the scissors.

12. The pair of scissors according to claim 11, wherein said nose part has a lower surface generally parallel with said straight back edge and spaced a second distance from, and in a direction generally perpendicular to, the cutting edge of the lower blade in a closed position of the scissors.

13. The pair of scissors according to claim 12 wherein a distal edge of said upper blade below said nose and extending said second distance is oriented to be substantially perpendicular to said upper blade back edge.

14. The pair of scissors according to claim 11 wherein said distal end of said back edge of said upper blade stands a distance above said cutting edge of said lower blade in the closed position of the scissors.

15. The pair of scissors according to claim 11 wherein a main part of said lower blade tapers toward said distal end which is provided with a rounded bulb.

16. The pair of scissors according to claim 15, wherein said bulb is joined with said tapered main part at a point generally aligned with a base of said nose part in the closed position of the scissors.

17. The pair of scissors according to claim 11 wherein said back edge of said lower blade is provided with a chamfer inwardly.

18. The pair of scissors according to claim 11 wherein said back edge of said lower blade is provided with an inwardly placed rounding.

19. The pair of scissors according to claim 11 wherein at least one of said cutting edges is provided with a non-slip surface.

20. The pair of scissors according to claim 11 wherein at least one of said cutting edges makes an angle of less than 75° with said plane.

* * * * *